United States Patent [19]

Tascher

[11] Patent Number: 4,653,542
[45] Date of Patent: Mar. 31, 1987

[54] MEDICAL TUBING AND CONNECTOR

[75] Inventor: Edward R. Tascher, Long Beach, Calif.

[73] Assignee: The Kendall Company, Boston, Mass.

[21] Appl. No.: 193,101

[22] Filed: Oct. 2, 1980

[51] Int. Cl.⁴ .............................................. F16L 47/00
[52] U.S. Cl. .................................. 138/109; 138/96 T; 138/122; 138/173; 138/178
[58] Field of Search ............... 138/109, 121, 122, 173, 138/96 T, 128

[56] References Cited

U.S. PATENT DOCUMENTS

| | | | |
|---|---|---|---|
| 704,233 | 7/1902 | Brown | 138/122 X |
| 1,302,300 | 4/1919 | Brinkman | 138/122 X |
| 2,062,188 | 11/1936 | Morphy | 138/173 X |
| 4,232,712 | 11/1980 | Squires | 138/109 |

Primary Examiner—James E. Bryant, III

[57] ABSTRACT

There is described an improved apparatus for use in medical applications. The invention is adaptable for either disposable or non-disposable use. The apparatus includes a tubing which has a spiral configuration and a "spin-in cuff" or connector with a spiral end which mates with the spiral tubing to form a connection which is secure, substantially fluid leakproof, and yet readily engageable and disengageable. The cuff (or connector) is adapted to interact with existing medical equipment.

9 Claims, 5 Drawing Figures

MEDICAL TUBING AND CONNECTOR

BACKGROUND

1. Field of the Invention. This invention is directed to equipment which is especially useful in the medical or hospital applications, in general, and, more particularly, to an improved tubing and connector which is used with anesthesia, respiratory therapy or other similar hospital uses.

2. Prior Art. In the medical and hospital professions, there are many applications for tubing which is used in patient care as well as in other activities. For example, tubing is used in the anesthesia process between the patient and the appropriate material sources (e.g., pressurized tanks). Likewise, tubing is frequently used in catheter applications to drain body fluids from the patient to a suitable receptacle. In other applications, intravenous (IV) applications of fluids to the patient are provided. In the present-day environment, much of this tubing and its associated couplers and the like are made to be disposable in order to avoid infection, cross-contamination, reduce maintenance costs, and so forth. In addition, it is highly desirable to combine a "modular" type of tubing system so that the operating personnel can function more smoothly and easily. Moreover, in case of emergency, an easily and readily adaptable and useful tubing apparatus is highly desirable.

There are several types of tubing which are currently available as described hereinafter, which have significant problems or drawbacks. Consequently, it is highly desirable to obtain an improved apparatus for use in the medical and/or hospital applications, a few of which are noted above.

SUMMARY OF THE INVENTION

The invention is directed to medical tubing which has a spiral configuration and a cuff, or end adaptor, which is used therewith. The adaptor or cuff includes an end portion which is threaded in a manner to mate with the spiral configuration of the tubing. The spiral configuration provides a secure seal between the cuff and the tubing. In addition, the spiral/thread configuration permits easy engagement and/or disengagement of the cuff adaptor relative to the tubing. In addition, the tubing can be cut to virtually any length without any difficulty in interconnection of the tubing and the cuff adaptor.

DESCRIPTION OF A PREFERRED EMBODIMENT

Figure 1:
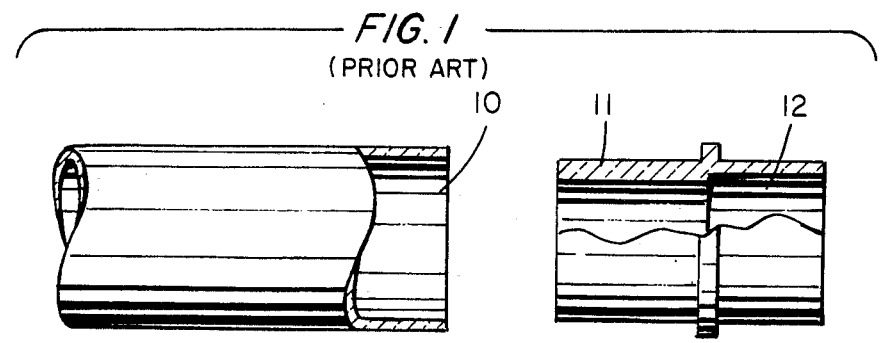
FIG. 1 is a schematic diagram of one type of tubing and adaptor which is known in the prior art.

Referring first to FIG. 1, there is shown a diagram which represents one type of tubing and adaptor known in the prior art. In FIG. 1, tube 10 is a "straight" tube which may be formed of a suitable plastic or the like and which has a smooth exterior surface as well as a smooth interior surface. Tube 10 can be of any length or diameter. The cuff or end adaptor includes an insert portion 11 which is inserted into the tubing 10. The outer diameter of insert 11 is arranged to snugly engage the internal surface of tubing 10. The end portion 12 of the adaptor is of any appropriate diameter to mate with the equipment to which the tubing is to be connected. Insert portion 11 and end portion 12 both have generally smooth interior and exterior surfaces.

This type of tubing and connector or coupling are probably the simplest type of apparatus in terms of configuration. Tubing 10 and insert portion 11 fit together snugly while end portion 12 of the adaptor fits snugly to the apparatus involved. However, in order to assure a secure connection, the outer diameter of insert 11 and the inner diameter of tubing 10 require a snug, force-fit connection. Obviously, if a loose fit is obtained a poor connection is provided wherein leakage can occur or the coupling can come apart. On the other hand, if insert 11 is slightly larger than desirable, a fit cannot be accomplished at all. Even in those cases where components with the appropriate dimensions are provided, a very difficult task is presented to the operator in causing tubing 10 to engage insert 11. Similarly, this force-fit creates substantial friction and is not readily disengageable in emergency either. Consequently, this type of connection is not fully desirable in many applications.

Figure 2:
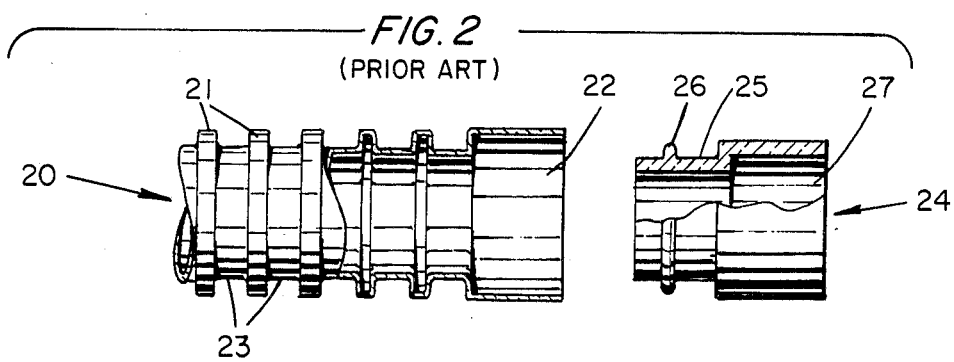
FIG. 2 is a schematic diagram of another type of tubing and adaptor which is known in the prior art.

Referring now to FIG. 2, there is shown another embodiment of the tubing and connectors which are known in the prior art. In this instance, tube 20 includes a plurality of disc-like annular members 21 connected together by a basic channel 23. The end of tube 20 includes an elongated cuff member 22. The end adaptor 24 includes the end cuff 27 which is used to be connected to the equipment in a similar fashion to end adaptor 12 shown in FIG. 1. In addition, the cuff or adaptor 24 includes an annular disc 26 formed on the basic insert portion 25. In this instance, end member 22 is spread apart and insert portion 25 with annular disc 26 is inserted therein until disc 26 engages with one of the annular grooves 21 in tube 20. It is clear that this relationship provides a secure junction and connection which is unlikely to come apart and also unlikely to leak. However, it is manifestly obvious that once the disc 26 is locked into the recess in groove 21, it will be virtually impossible to remove cuff adaptor 24 from tube 20 without seriously damaging or diminishing the integrity of the end cap 22 of tubing 20. Once the integrity of end cap 22 is damaged or diminished, the effect and efficacy of the connector shown in FIG. 2 is seriously suspect. Moreover, it is clear that this connection does not permit ready engagement and/or disengagement and is undesirable in emergency operations.

Figure 3:
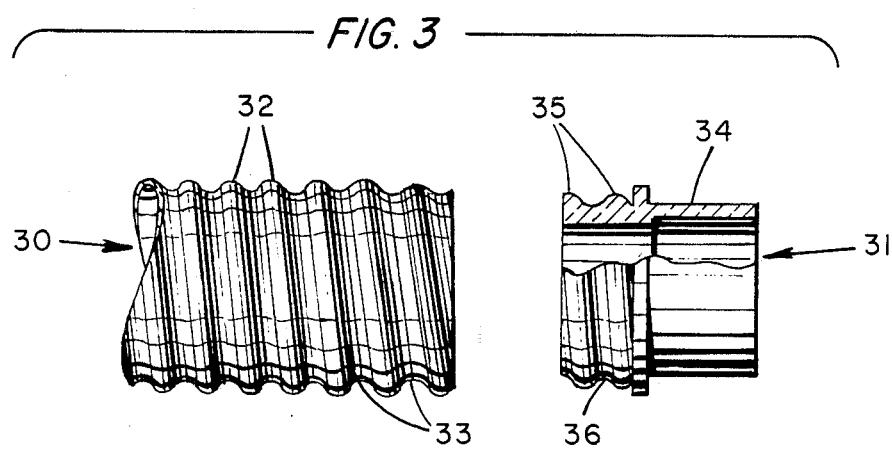
FIG. 3 is a schemtic representation of the tubing and adaptor of the instant invention.

Referring now to FIG. 3, there is shown a preferred embodiment of the instant invention. In this instance, tubing 30 is formed in the configuration of a spiral which has the appearance of a screw thread arrangement. The spiral tubing 30 includes a plurality of crests 32 joined together by roots 33 which form a continuous spiral tube.

End cap 31 includes the adaptor cap 34 which is used to connect the apparatus to other equipment as described relative to the devices shown in FIGS. 1 and 2. In addition, the insert portion of end cap 31 includes a threaded or spiral configuration, as well. In this case, the insert portion includes the crests 35 and the roots 36.

The threaded portion of end cap 31 is specifically arranged to intimately mate with the spiral portion of tubing 30. Thus, the insert end of end cap 31 is screwed into tubing 30 with the grooves and crests matching appropriately. It is clear that this type of mating arrangement provides a basically leak-proof, secure seal. That is, fluid traversing through tubing 30 and end cap 31 (in either direction) is not likely to leak at the connection point. In addition, the threaded arrangement is such that the connection is inhibited from accidentally or inadvertently decoupling when bumped or tugged as could occur in the case of the prior art device shown in FIG. 1.

In addition, the spin-in or screw-in arrangement of the connecton is much simpler to effect, both from the engagement and disengagement aspect, than is the case in the prior art device shown in FIG. 2. However, the instant invention has the same, if not greater, security and integrity of the connection.

Figures 4, 5:
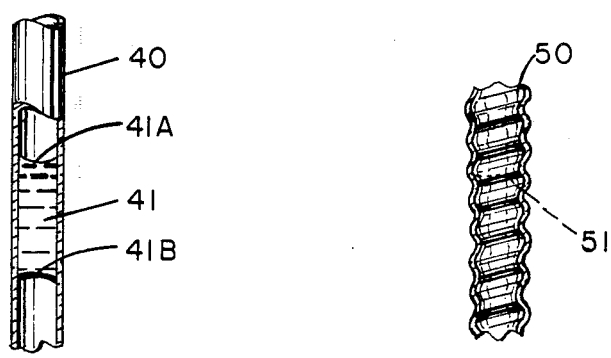
FIG. 4 is a cross-sectional view of a prior art tubing with a meniscus blockage.
FIG. 5 is a cross-section of the tubing of the instant invention which shows the avoidance of a meniscus blockage.

Referring now to FIG. 4, there is shown a schematic representation of a meniscus blockage which frequently occurs in tubes known in the prior art. In this case, a tube 40 is depicted. This tube 40 may be very similar to tube 10 in FIG. 1 or to portions of tube 20 in FIG. 2. In either event, tube 40 has an essentially continuous, smooth inner surface. A fluid passing through tube 40 can frequently develop a meniscus 41A which creates a surface tension and essentially an adhesion between the fluid 41 and the inner surface of the tube wall 40. In this case, the fluid 41 may be retained in the tube 40, thereby blocking the tube. This can be a problem in many cases, such as IV applications, catheterization, or the like, and is highly undesirable.

Referring now to FIG. 5, there is shown a cross-sectional view of tubing 50 which has a spiral configuration such as tube 30 in FIG. 3. In the cross-sectional view, it is seen that the spiral configuration essentially prevents the formation of a meniscus. A dashed line 51 is depicted to represent the position of a hypothetical meniscus. It is clear that there is no occasion in the spiral tube 50 where a straight-wall configuration of the tubing exists. Inasmuch as there is no such straight-wall configuration, the surface tension and adhesion which is required to form a meniscus does not occur. Consequently, a meniscus is not formed and the blockage cannot occur.

Thus, there has been shown and described a preferred embodiment of the instant invention. While only one illustrative drawing is presented, it must be understood that the spiral tubing and associated end can have different sizes and/or configurations. That is, the spiral can be more tightly wound or more loosely wound. The diameters of the tubing and the end cap can vary. This tubing concept is equally applicable to small capillary-type tubing or to very large diameter tubing. In a preferred embodiment, the tubing and the cap are formed of polyolefin, but other types of material can be utilized.

The tubing should be flexible (bendable) but not soft (collapsible). Of course, the material should be inert relative to the application for which it is proposed and the materials (e.g., gases) with which it is to be used. The length of tubing 30 is virtually immaterial to the instant invention. That is, by cutting the tubing at any location or length, a thread-in spiral is maintained at either end of the tubing.

The specific design and materials noted above are intended to be illustrative only. It is clear that other modifications to the configuration (for example, the thread or the spiral direction can be reversed) which fall within the purview of this description are intended to be included therein as well. The scope of this invention is limited only by the claims appended hereto.

Having thus described a preferred embodiment, what is claimed is:

1. Improved tubing comprising,
   an elongated tube having a relatively thin wall,
   said tube being flexible and substantially permanently formed in a spiral configuration along substantially the entire length thereof so that both the inner and outer surfaces of the tube exhibit the spiral configuration,
   said spiral configuration including crests and roots of different diameters, and
   a coupling member adapted to selectively engage an end of said elongated tube,
   said coupling member having at least one end thereof substantially permanently formed in a spiral configuration so that said one end can be threadedly engaged with said tube.
2. The tubing recited in claim 1 wherein,
   said tube is formed of a polyolefin plastic.
3. The tubing recited in claim 1 wherein,
   said coupling member has at least two spiral convolutions which engage said tube in a leak-proof manner.
4. The tubing recited in claim 1 wherein,
   said spiral tube has no flat surfaces throughout its entire length.
5. The tubing recited in claim 1 wherein,
   said tube is flexible but not soft.
6. The tubing recited in claim 1 wherein,
   said coupling member includes at least one end thereof which is substantially smooth.
7. The tubing recited in claim 5 wherein,
   said tube configuration is generally not temperature sensitive.
8. The tubing recited in claim 1 wherein,
   said spiral configuration of said tube and the spiral configuration at said one end of said coupling member mate securely.
9. The tubing recited in claim 1 wherein,
   said spiral configuration prevents the forming of a meniscus on a fluid flowing through said tubing.

* * * * *